United States Patent [19]
Douillet et al.

[11] Patent Number: 6,043,251
[45] Date of Patent: Mar. 28, 2000

[54] USE OF 1-(2-NAPHTH-2-YLETHYL)-4-(3-TRIFLUOROMETHYLPHENYL)-1,2,3,6-TETRAHYDROPYRIDINE FOR PREPARING DRUGS FOR TREATING AMYOTROPHIC LATERAL SCLEROSIS

[75] Inventors: Patrice Douillet, St.-Gely-du-Fesc; Jacqueline Fournier, Plaisance-du-Touch, both of France

[73] Assignee: Sanofi, France

[21] Appl. No.: 09/051,740

[22] PCT Filed: Oct. 25, 1996

[86] PCT No.: PCT/FR96/01674

§ 371 Date: Sep. 14, 1998

§ 102(e) Date: Sep. 14, 1998

[87] PCT Pub. No.: WO97/15304

PCT Pub. Date: May 1, 1997

[30] Foreign Application Priority Data

Oct. 26, 1995 [FR] France .................................. 95 12635
Jun. 13, 1996 [FR] France .................................. 96 07336

[51] Int. Cl.[7] .......................... A61K 31/44; A61K 38/30; A61K 38/18; A61K 31/425
[52] U.S. Cl. .......................... 514/277; 514/315; 514/317; 514/319; 514/365; 514/367; 514/12
[58] Field of Search .................................. 514/277, 315, 514/317, 319, 365, 367, 12

[56] References Cited

U.S. PATENT DOCUMENTS

| | | |
|---|---|---|
| 5,229,389 | 7/1993 | Coude et al. . |
| 5,270,320 | 12/1993 | Coude et al. . |
| 5,292,745 | 3/1994 | Heaulme et al. . |
| 5,468,753 | 11/1995 | Coude et al. . |
| 5,527,814 | 6/1996 | Louvel . |

FOREIGN PATENT DOCUMENTS

| | | |
|---|---|---|
| 0458696 | 5/1991 | European Pat. Off. . |
| 0498718 | 5/1992 | European Pat. Off. . |
| 0558861 | 10/1992 | European Pat. Off. . |

OTHER PUBLICATIONS

"Safety and Efficacy Controlled Trial of SR 57746A in Amyotrophic Lateral Sclerosis", L. Lacomblez et al., *Congress of the Spanish Society of Pharmacology*, Sep. 1996, Granada, p. 206.

"A Phase I/II Study of Recombinant Human Brain–Derived Neurotrophic Factor in Patients with Amyotrophic Lateral Sclerosis", W. G. Bradley et al., *Annals of Neurology*, vol. 38, No. 6, 1996, p. 971.

"Brain–Derived Neurotrophic Factor Rescues Spinal Motor Neurons from Axotomy–Induced Cell Death", Q. Yan et al., *Nature*, vol. 360, 1992, pp. 753–759.

"Protective Effects of SR 57746A in Central and Peripheral models of Neurodegenerative Disorders in Rodents and Primates", J. Fournier et al., *Neuroscience*, vol. 55, No. 3, 1993, pp. 629–641.

"SR 57746A: Inductio of NGF Gene Expression and Synthesis in astrocytoma and Fibroblast Cell Lines and Beneficial Effects in a Peripheral Degenerative Model in Rats", T. Gauthier et al., *Fundamental & Clinical Pharmacology*, vol. 7, No. 7, 1993. p. 359.

"Neurotrophic Factor Therapy for Nervous System Degenerative Diseases", F. Hefti, *Journal of Neurobiology*, vol. 25, No. 11, 1994, pp. 1418–1435.

"Clinical Application of Cell Transplantation and Neurotrophic Factors in CNS Disorders", O. Lindvall et al., *Current Opinion in Neurobiology*, vol. 4, No. 5, 1994, pp. 752–757.

"Experimental Rationale for the Therapeutic Use of Neurothrophins in Amyotrophic Lateral Sclerosis", J.L. Seeburger et al., *Experimental Neurology*, vol. 124, No. 1, 1993, pp. 64–72.

*Primary Examiner*—Keith D. MacMillan
*Attorney, Agent, or Firm*—Michael D. Alexander; Paul E. Dupont

[57] ABSTRACT

The present invention relates to the use of 1-(2-naphth-2-ylethyl)-4-(3-trifluoromethylphenyl)-1,2,3,6-tetrahydropyridine or its addition salts with pharmaceutically acceptable acids for the preparation of drugs intended for the treatment of amyotrophic lateral sclerosis (ALS).

19 Claims, No Drawings

USE OF 1-(2-NAPHTH-2-YLETHYL)-4-(3-TRIFLUOROMETHYLPHENYL)-1,2,3,6-TETRAHYDROPYRIDINE FOR PREPARING DRUGS FOR TREATING AMYOTROPHIC LATERAL SCLEROSIS

The present invention relates to the use of 1-(2-naphth-2-ylethyl)4-(3-trifluoromethylphenyl)-1,2,3,6-tetrahydropyridine or its addition salts with pharmaceutically acceptable acids for the preparation of drugs intended for the treatment of amyotrophic lateral sclerosis (ALS).

ALS is a serious progressive motor neuron disease which causes muscular atrophy and most often develops in a few years into a fatal respiratory insufficiency.

Very few products are being studied for ALS, particular examples being peptide compounds such as IGF-1 (Insulin-like Growth Factor 1) and BDNF (Brain Derived Neurotrophic Factor), which are described in Annals of Neurology, 1995, 38, 971, and Nature, 1992, 360, 753–759.

The only non-peptide compound to have been tested for this disease is riluzole, whose chemical name is 2-amino-6-trifluoromethoxybenzothiazole, which is apparently capable of slowing down the progression of the disease in a particular group of subjects suffering from ALS (G. Bensimon et al., N. Engl. J. Med., 1994, 330, 585–591; Scrip, 1995, No. 2035:21), but no product effective in the treatment of this disease is currently available on the pharmaceutical market. According to the article by G. Bensimon et al. cited above, riluzole prolongs the survival of patients suffering from ALS, but the side effects, such as asthenia, spasticity and an increase in the transaminase levels, impair the quality of life of said patients.

EP-A-458696 describes the use of 1-(2-naphth-2-ylethyl) 4-(3-trifluoromethylphenyl)-1,2,3,6-tetrahydropyridine, called SR 57746 in the literature, for the preparation of drugs intended for combating neurodegenerative states. In said document the neurotrophic activity of SR 57746 is indicated as being useful in memory disorders, vascular dementia, postencephalitic disorders, postapoplectic disorders, post-traumatic syndromes due to a cranial traumatism, disorders derived from cerebral anoxia, Alzheimer's disease, senile dementia, subcortical dementia such as Huntington's chorea and Parkinson's disease, dementia caused by AIDS, neuropathy derived from morbidity or from damage to the sympathetic or sensory nerves, brain diseases such as cerebral edema, and spinocerebellar degenerations.

The neurotrophic action of SR 57746 on the nervous system is similar to that of NGF, Nerve Growth Factor (EP-A-458696), and, in particular, is said to provide neuroprotection by inducing the effects of the NGF system (J. Fournier, Neuroscience, 1993, 55(3), 629–641).

It has now been found that the administration of SR 57746 or one of its addition salts with pharmaceutically acceptable acids significantly slows down the progression of ALS while at the same time improving the patients' quality of life. This therapeutic action of SR 57746 is not associated with the release of NGF since the latter is not said to be a trophic factor for the motor neurons, as indicated for example in Neuron, 1988, 1(4), 335–43; J. Comp. Neurol., 1982, 210/2, 174–189; and Eur. J. Neurosci., 1993, 5(5), 466–474.

The activity of SR 57746 in the treatment of ALS is therefore unexpected.

Thus, according to one of its aspects, the present invention relates to the use of 1-(2-naphth-2-ylethyl)-4-(3-trifluoromethylphenyl)-1,2,3,6-tetrahydropyridine or one of its addition salts with pharmaceutically acceptable acids for the preparation of drugs intended for the treatment of amyotrophic lateral sclerosis.

The clinical activity of SR 57746 in this disease was demonstrated by means of a study performed to evaluate the activity indices on the clinical and functional signs of ALS and to evaluate tolerance after the prolonged administration of 1-(2-naphth-2-ylethyl)-4-(3-trifluoromethylphenyl)- 1,2,3,6-tetrahydropyridine hydrochloride (SR 57746 A).

In this randomized double-blind clinical study, 54 patients received SR 57746 A orally at a dose corresponding to 2 mg/day of the free base, for a period of 8 months. The doses indicated in the present description always refer to the amount of free base administered or contained in the dosage unit.

Several variables were taken into account in evaluating said activity of SR 57746 A in the treatment of ALS, especially:

a vital capacity test for measuring the maximum respiratory capacity;

a muscle test for evaluating the muscular strength;

a neurological examination for evaluating the reflexes; and

Norris examinations (bulbar and limbs) for evaluating the patients' capacity to perform certain movements.

The evaluation of the efficacy of the compound under examination is expressed in the form of scores which indicate the state of progression of the disease in the patient compared with healthy subjects.

The results obtained show that, during the 8 months, the two treatment groups (2 mg/day of SR 57746 A and placebo) gradually show remarkable differences for the three principal variables studied: respiratory vital capacity, muscular strength and Norris functional scales.

The means of the development slopes of the patients treated for 8 months with SR 57746 A are of the order of 40% lower than those of the patients treated with placebo.

The results obtained by this study show that SR 57746 A is capable of significantly slowing down the progression of ALS. The product is also very well tolerated, as was observed during the 8 months of treatment.

According to another of its aspects, the present invention relates to a method of treating amyotrophic lateral sclerosis which comprises administering an effective dose of 1-(2-naphth-2-ylethyl)4-(3-trifluoromethylphenyl)-1,2,3,6-tetrahydropyridine or one of its addition salts with pharmaceutically acceptable acids to patients suffering from this disease.

According to the present invention, SR 57746 can be administered on its own or in association with other active principles, especially with riluzole in combination therapy or in the same pharmaceutical form.

More particularly, the present invention relates to the use of 1-2-naphth-2-ylethyl)-4-(3-trifluoromethylphenyl)-1,2,3, 6-tetrahydropyridine and 2-amino-6-trifluoromethoxybenzothiazole or their addition salts with pharmaceutically acceptable acids for the preparation of a drug intended for the treatment of amyotrophic lateral sclerosis.

The pharmaceutical compositions containing an association of SR 57746 and riluzole or their pharmaceutically acceptable salts, and the use of said association for the preparation of drugs intended for the treatment of amyotrophic lateral sclerosis, constitute further aspects of the present invention.

Thus the present invention also relates to a pharmaceutical composition in which 1-(2-naphth-2-ylethyl)-4-(3-trifluoromethylphenyl)-1,2,3,6-tetrahydropyridine and 2-amino-6-trifluoromethoxybenzothiazole or their addition salts with pharmaceutically acceptable acids are present as the active principles.

Other compositions contain SR 57746 and protein growth factors such as IGF-1 (Insulin-like Growth Factor) and BDNF (Brain Derived Neurotrophic Factor), which are active in the treatment of ALS.

Thus, according to another of its aspects, the invention relates to the use of 1-(2-naphth-2-ylethyl)4-(3-trifluoromethylphenyl)- 1,2,3,6-tetrahydropyridine or one of its addition salts with pharmaceutically acceptable acids for the preparation of drugs intended for the treatment of amyotrophic lateral sclerosis, in association with another active principle selected from BDNF, IGF-1 and their pharmaceutically acceptable salts.

According to another aspect, the present invention also relates to a method of treating ALS which consists in administering, to a patient suffering from this disease, an effective dose of 1-(2-naphth-2-ylethyl)-4-(3-trifluoromethylphenyl)-1,2,3,6-tetrahydropyridine or one of its addition salts with pharmaceutically acceptable acids and an effective dose of 2-amino-6-trifluoromethoxybenzothiazole or one of its addition salts with pharmaceutically acceptable acids, said administrations being simultaneous, sequential or over a period of time.

According to another of its aspects, the invention also relates to a method of treating ALS which consists in administering, to a patient suffering from this disease, an effective dose of 1-(2-naphth-2-ylethyl)4-(3-trifluoromethylphenyl)-1,2,3,6-tetrahydropyridine or one of its addition salts with pharmaceutically acceptable acids and an effective dose of another active principle selected from BDNF, IGF-1 and their pharmaceutically acceptable salts, said administrations being simultaneous, sequential or over a period of time.

According to another aspect, the invention also relates to a kit intended for the treatment of ALS which contains:

(a) one or more unit doses of 1-(2-naphth-2-ylethyl)-4-(3-trifluoromethylphenyl)-1,2,3,6-tetrahydropyridine or one of its pharmaceutically acceptable salts; and (b) one or more unit doses of 2-amino-6-trifluoromethoxybenzothiazole, BDNF, IGF-1 or one of their pharmaceutically acceptable salts, said kit being intended for administering the components (a) and (b) simultaneously, sequentially or over a period of time.

SR 57746 and its addition salts with pharmaceutically acceptable acids are preferably administered orally.

In the pharmaceutical compositions of the present invention for oral administration, SR 57746 or a pharmaceutically acceptable salt thereof, used as the active principle, can be administered to animals and humans in unit forms of administration mixed with conventional pharmaceutical carriers, for the treatment of the above-mentioned complaints. The appropriate unit forms of administration include for example tablets, which may be divisible, gelatin capsules, powders, granules and solutions or suspensions to be taken orally.

When a solid composition is prepared in the form of tablets, the main active ingredient is mixed with a pharmaceutical vehicle such as gelatin, starch, lactose, magnesium stearate, talcum, gum arabic or the like. The tablets can be coated with sucrose or other appropriate substances, or else they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methylparaben and propylparaben as antiseptics, a flavoring and an appropriate color.

The water-dispersible powders or granules can contain the active ingredient mixed with dispersants or wetting agents or with suspending agents such as polyvinylpyrrolidone, as well as with sweeteners or taste correctors.

The active principle can also be formulated as microcapsules, optionally with one or more carriers or additives.

In the pharmaceutical compositions according to the present invention, the active principle can also be in the form of an inclusion complex in cyclodextrins, their ethers or their esters.

The amount of active principle to be administered depends, as always, on how advanced the disease is and on the patient's age and weight. Nevertheless the unit doses generally comprise from 0.5 to 10 mg, advantageously from 1 to 5 and preferably from 1 to 3 mg, for example 1, 1.5, 2, 2.5 or 3 mg, of active principle. These unit doses are normally administered one or more times a day, preferably one to three times a day, the overall dose in humans varying between 0.5 and 50 mg per day, for example from 1 to 20 mg per day.

When SR 57746 is administered in association with other active principles, especially with riluzole, the doses are selected from the doses which would be administered for each drug, depending on the severity of the disease and the patient's age and weight. Advantageous associations contain from 0.5 to 10 mg of SR 57746 or one of its pharmaceutically acceptable salts and from 30 to 100 mg of riluzole or one of its pharmaceutically acceptable salts, per dosage unit, particular preference being given to those containing 0.5 mg of SR 57746 or one of its pharmaceutically acceptable salts and 50 mg of riluzole or one of its pharmaceutically acceptable salts, 1 mg of SR 57746 or one of its pharmaceutically acceptable salts and 50 mg of riluzole or one of its pharmaceutically acceptable salts, 1.5 mg of SR 57746 or one of its pharmaceutically acceptable salts and 50 mg of riluzole or one of its pharmaceutically acceptable salts, or 2 mg of SR 57746 or one of its pharmaceutically acceptable salts and 50 mg of riluzole or one of its pharmaceutically acceptable salts, per dosage unit, mixed with a pharmaceutical excipient These dosage units can be administered 1 or 2 times a day.

The following non-limiting Examples illustrate the invention.

EXAMPLES 1 to 3

Gelatin capsules are prepared which contain 0.5 mg, 1 mg or 2 mg of SR 57746 (prepared as described in EP-A-0 101 381).

The product SR 57746 A is sieved through a 0.200 mm mesh and then premixed with the excipients. This mixture is sieved through a 0.315 mm mesh, remixed and then sieved again through a 0.315 mm mesh. After a final mixing, the gelatin capsules are filled.

| | | | |
|---|---|---|---|
| SR 57746 A | 0.548 mg | 1.096 mg | 2.192 mg |
| Modified corn starch | 142.852 mg | 142.304 mg | 141.208 mg |
| Microcrystalline cellulose | 26.0 mg | 26.0 mg | 26.0 mg |
| Anhydrous colloidal silica | 0.20 mg | 0.20 mg | 0.20 mg |
| Magnesium stearate | 0.40 mg | 0.40 mg | 0.40 mg |

What is claimed is:

1. A method of treating amyotrophic lateral sclerosis which comprises administering to a patient an effective amount of 1-(2-naphth-2-ylethyl)-4-(3-trifluoromethylphenyl)-1,2,3,6-tetrahydropyridine or one of its addition salts with pharmaceutically acceptable acids.

2. A method according to claim 1 wherein the acid addition salt is the hydrochloride.

3. A method according to claim 1 wherein 1-(2-naphth-2-ylethyl)-4-(3-trifluoromethylphenyl)-1,2,3,6-tetrahydropyridine or one of its addition salts is administered as a pharmaceutical composition in the form of a unit dosage.

4. A method according to claim 3 wherein the unit dosage form comprises from 0.5 to 10 mg of 1-(2-naphth-2-ylethyl)-4-(3-trifluoromethylphenyl)-1,2,3,6-tetrahydropyridine or one of its addition salts.

5. A method according to claim 4 wherein the unit dosage form comprises from 1 to 5 mg of 1-(2-naphth-2-ylethyl)-4-(3-trifluoromethylphenyl)-1,2,3,6-tetrahydropyridine or one of its addition salts.

6. A method according to claim 3 wherein the pharmaceutical composition is in the form of a composition for oral administration.

7. A method of treating amyotrophic lateral sclerosis which comprises administering to a patient an effective amount of 1-(2-naphth-2-ylethyl)-4-(3-trifluoromethylphenyl)-1,2,3,6-tetrahydropyridine and an effective amount of 2-amino-6-trifluoromethoxybenzothiazole or their addition salts with pharmaceutically acceptable acids.

8. A pharmaceutical composition comprising 1-(2-naphth-2-ylethyl)-4-(3-trifluoromethylphenyl)-1,2,3,6-tetrahydropyridine and 2-amino-6-trifluoromethoxybenzothiazole or their addition salts with pharmaceutically acceptable acids as the active principles.

9. A pharmaceutical composition according to claim 8 containing from 0.5 to 10 mg of 1-(2-naphth-2-ylethyl)-4-(3-trifluoromethylphenyl)-1,2,3,6-tetrahydropyridine and from 30 to 100 mg of 2-amino-6-trifluoromethoxybenzothiazole or their addition salts with pharmaceutically acceptable acids.

10. A pharmaceutical composition according to claim 9 containing 0.5 mg of 1-(2-naphth-2-ylethyl)-4-(3-trifluoromethylphenyl)-1,2,3,6-tetrahydropyridine and 50 mg of 2-amino-6-trifluoromethoxybenzothiazole or their addition salts with pharmaceutically acceptable acids.

11. A pharmaceutical composition according to claim 9 containing 1 mg of 1-(2-naphth-2-ylethyl)-4-(3-trifluoromethylphenyl)- 1,2,3,6-tetrahydropyridine and 50 mg of 2-amino-6-trifluoromethoxybenzothiazole or their addition salts with pharmaceutically acceptable acids.

12. A pharmaceutical composition according to claim 9 containing 1.5 mg of 1-(2-naphth-2-ylethyl)-4-(3-trifluoromethylphenyl)-1,2,3,6-tetrahydropyridine and 50 mg of 2-amino-6-trifluoromethoxybenzothiazole or their addition salts with pharmaceutically acceptable acids.

13. A pharmaceutical composition according to claim 9 containing 2 mg of 1-(2-naphth-2-ylethyl)-4-(3-trifluoromethylphenyl)-1,2,3,6-tetrahydropyridine and 50 mg of 2-amino-6-trifluoromethoxybenzothiazole or their addition salts with pharmaceutically acceptable acids.

14. A method of treating amyotrophic lateral sclerosis which comprises administering to a patient an effective amount of 1-(2-naphth-2-ylethyl)-4-(3-trifluoromethylphenyl)-1,2,3,6-tetrahydropyridine or its addition salts with pharmaceutically acceptable acids in association with another active principle selected from BDNF, IGF-1 and their pharmaceutically acceptable salts.

15. A pharmaceutical composition containing 1-(2-naphth-2-ylethyl)-4-(3-trifluoromethylphenyl)-1,2,3,6-tetrahydropyridine and another active principle selected from BDNF, IGF-1 and their pharmaceutically acceptable salts.

16. A method according to claim 1 wherein the effective dose of 1-(2-naphth-2-ylethyl)-4-(3-trifluoromethylphenyl)-1,2,3,6-tetrahydropyridine or one of its addition salts with pharmaceutically acceptable acids is 0.5 to 50 mg per day.

17. A method according to claim 1 wherein the administration of the effective dose of 1-(2-naphth-2-ylethyl)-4-(3-trifluoromethylphenyl)-1,2,3,6-tetrahydropyridine or one of its addition salts with pharmaceutically acceptable acids is effected at the same time as the administration of an effective dose of 2-amino-6-trifluoromethoxybenzothiazole or one of its addition salts with pharmaceutically acceptable acids.

18. A method according to claim 17 wherein the effective dose of 1-(2-naphth-2-ylethyl)-4-(3-trifluoromethylphenyl)-1,2,3,6-tetrahydropyridine or one of its addition salts with pharmaceutically acceptable acids and the effective dose of 2-amino-6-trifluoromethoxybenzothiazole or one of its addition salts with pharmaceutically acceptable acids are combined in the same pharmaceutical composition.

19. A method according to claim 1 wherein the administration of the effective dose of 1-(2-naphth-2-ylethyl)-4-(3-trifluoromethylphenyl)-1,2,3,6-tetrahydropyridine or one of its addition salts with pharmaceutically acceptable acids is effected at the same time as the administration of an effective dose of another active principle selected from BDNF, IGF-1 and their pharmaceutically acceptable salts.

\* \* \* \* \*